United States Patent [19]
Ben-Hur et al.

[11] Patent Number: 6,159,733
[45] Date of Patent: Dec. 12, 2000

[54] METHOD FOR PHOTOINACTIVATING MALIGNANT CELLS

[75] Inventors: Ehud Ben-Hur, New York, N.Y.; Robert A. Preti, Richfield, Conn.; Jan F. Keij, Los Alamos, N. Mex.

[73] Assignee: New York Blood Center, Inc., New York, N.Y.

[21] Appl. No.: 08/667,123

[22] Filed: Jun. 20, 1996

[51] Int. Cl.$^7$ .............................. C12N 5/00; C12N 9/02; A01N 55/00; C12Q 1/26
[52] U.S. Cl. .......................... 435/347; 514/63; 435/325; 435/25; 435/189
[58] Field of Search ............................ 514/63; 435/325; 435/347, 25, 189

[56] References Cited

U.S. PATENT DOCUMENTS

| | | | |
|---|---|---|---|
| 5,109,016 | 4/1992 | Dixon et al. | 514/410 |
| 5,120,649 | 6/1992 | Horowitz et al. | 435/173 |
| 5,232,844 | 8/1993 | Horowitz et al. | 435/173.1 |
| 5,281,616 | 1/1994 | Dixon et al. | 514/410 |
| 5,407,808 | 4/1995 | Halling et al. | 435/34 |
| 5,484,803 | 1/1996 | Richter | 514/410 |
| 5,516,629 | 5/1996 | Park et al. | 435/2 |

OTHER PUBLICATIONS

Levy, JG et al., "Selective Elimination of Malignant Stem Cells Using Photosensitizers Followed by Light Treatment", *Stem Cells* 1995 13:336–343.

Lum, LG et al., "The Immunoregulatory Effects of Merocyanine 540 on In Vitro Human T–and B–Lymphocyte Functions", *Blood* 1991 77(12):2701–2706.

Mulroney, CM et al., "The Use of Photodynamic Therapy in Bone Marrow Purging", *Seminars in Oncology* 1994 21(6):24–27.

Jamieson, C et al., "Efficacy of Benzoporphyrin Derivative, A Photosensitizer, in Selective Destruction of Leukemia Cells Using a Murine Tumor Model", *Exp Hematol* 1993 21:629–634.

Smith, OM et al., "Photodamaging Effects of Merocyanine 540 on Neurophils and HL–60 Cells", *Exp Hematol* 1992 20:1278–1284.

Lemoli, RM et al., "Dye–Mediated Photolysis is Capable of Eliminating Drug–Resistant (MDR+) Tumor Cells", *Blood* 1993 81(3):793–800.

Gulati, SC et al., "Is Bone Marrow Purging Providing to Be of Value?", *Oncology* 1994 8(9):19–32.

Itoh, T et al., "Merocyanine 540–Sensitized Photoinactivation of High–Grade Non–Hodgkin's Lymphoma Cells: Potential Application in Autologous BMT", *Bone Marrow Transplantation* 1993 12:191–196.

Qiu, K et al., "Merocyanine 540–Sensitized Photoinactivation of Leukemia Cells: Effects of Dose Fractionation", *Photochem Photobiol* 1992 56(4):489–493.

Köhler, A et al., "Investigation of the Usefulness of the Photodynamic Reaction for the Purging of Bone Marrow from Metastatic Neuroblastoma Cells", *J Photochem Photobiol* 1993 19:227–229.

Limoli, CL et al., "Response of Bromodeoxyuridine–Substituted Chinese Hamster Cells to UVA Light Exposure in the Presence of Hoechst Dye #33258: Survival and DNA Repair Studies", *Rad Res* 1994 138:312–319.

(List continued on next page.)

*Primary Examiner*—Hankyel Park
*Attorney, Agent, or Firm*—Amster, Rothstein & Ebenstein

[57] ABSTRACT

The present invention provides a method for photoinactivating malignant cells in a cell sample. The method comprises incubating the cell sample with a concentration of Pc 4 effective to cause a substantial number of the malignant cells contained in the cell sample to absorb Pc 4 such that upon application of a sufficient dose of red light, the Pc 4 absorbed malignant cells will be photoinactivated; and applying a sufficient dose of red light to the cell sample to photoinactivate the Pc 4 absorbed malignant cells contained in the cell sample.

7 Claims, 6 Drawing Sheets

OTHER PUBLICATIONS

Singer, CRJ et al., "Differential Phthalocyanine Photosensitization of Acute Myeloblastic Leukaemia Progenitor Cells: A Potential Purging Technique for Autologous Bone Marrow Transplantation", *Br J Haematol* 1988 68:417–422.

Lydaki, E et al., "Merocyanine 540 Mediated Photoirradiation of Leukemic Cells. In Vitro Inference on Cell Survival", *J Photochem Photobiol* 1996 32:27–32.

Sieber, F, "Elimination of Residual Tumor Cells From Autologous Bone Marrow Grafts by Dye–Mediated Photolysis: Preclinical Data", *Photochem Photobiol* 1987 46:71–76.

Preti, R.A., "Photolytic Purging of SK–BR3 and HL–60 Tumor Cells with the Phthalocyanin, Pc4", *J Hematotherapy* 1995 Jun. 20 4:246.

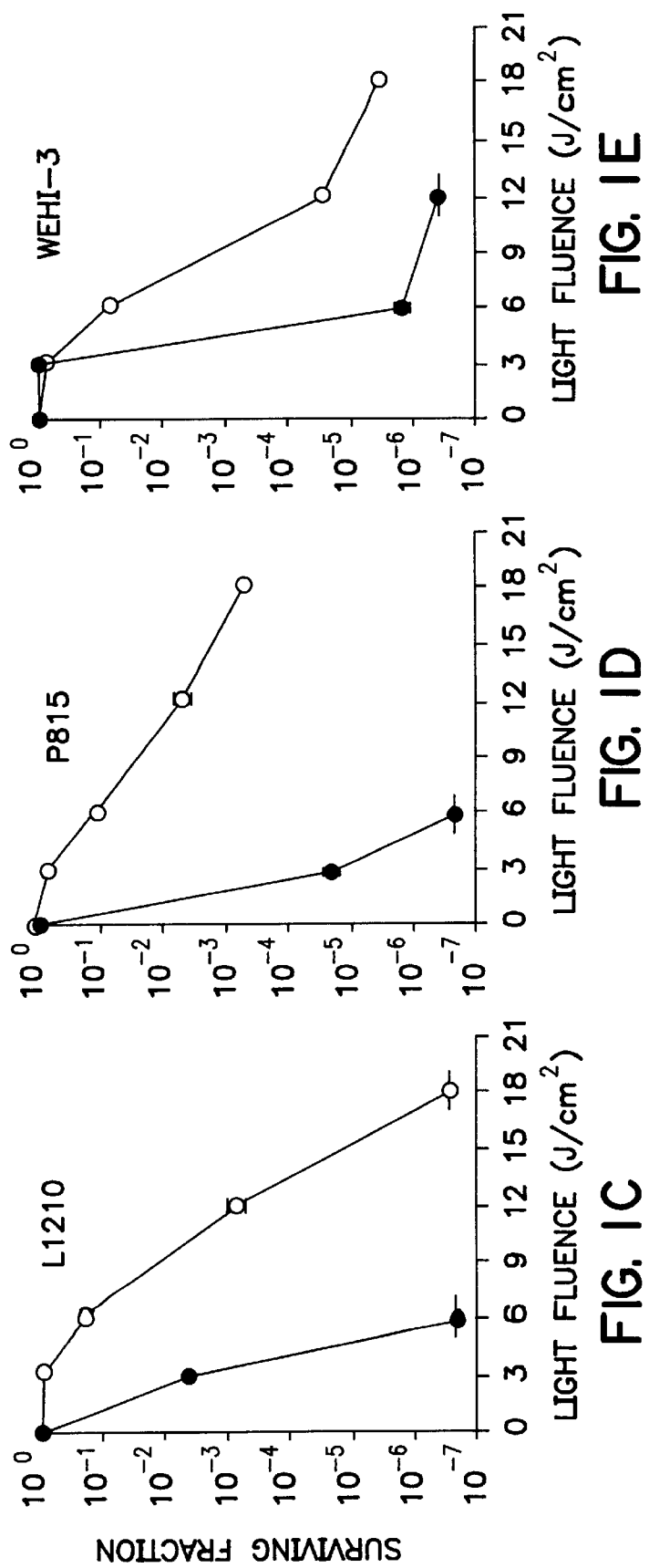

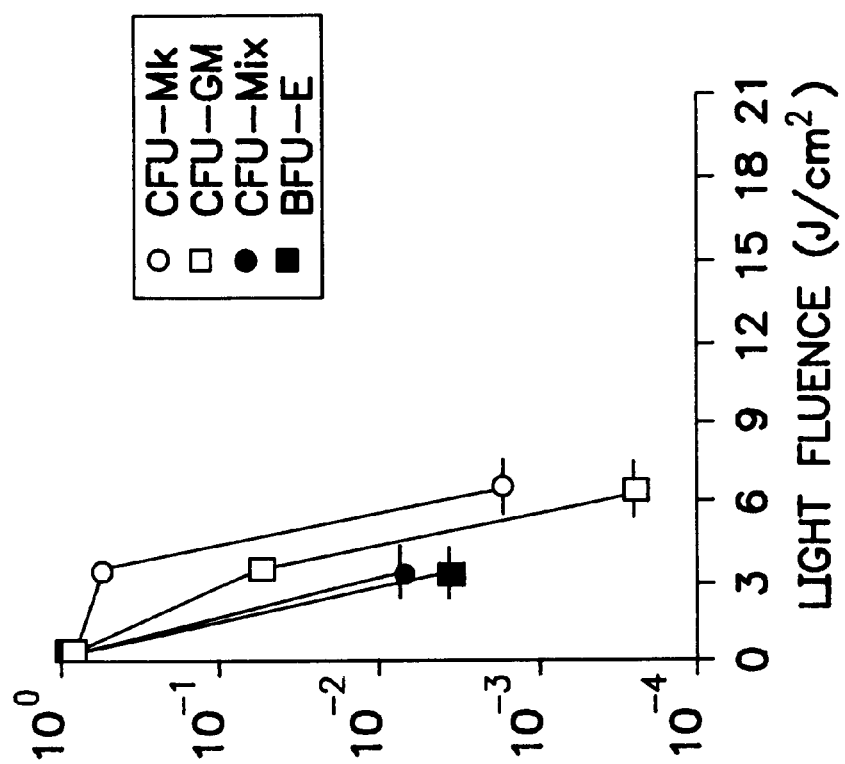
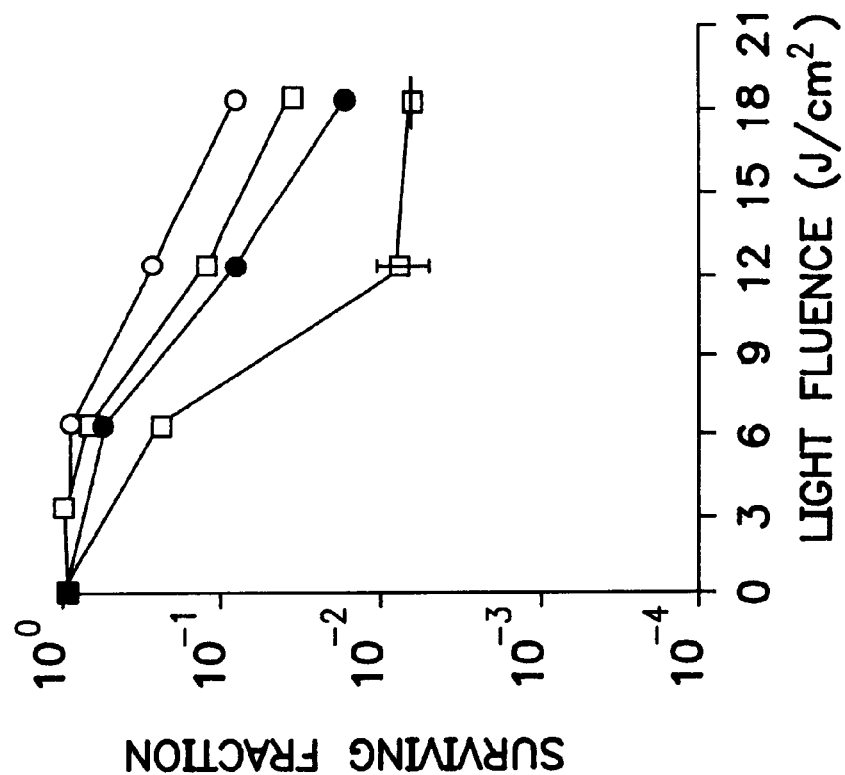
FIG. 2A
FIG. 2B

METHOD FOR PHOTOINACTIVATING MALIGNANT CELLS

BACKGROUND OF THE INVENTION

Low levels of contaminating malignant cells are present in autologous bone marrow (Simpson S. J., et al. *Blood* 23:1062 (1995)) of cancer patients and mobilized peripheral blood stem cell grafts (Brugger W., et al. *Blood* 83:636 (1994)). In some cases residual malignant cells have led to a relapse in the transplanted patients (Rill, D. R., et al. *Blood* 84:380 (1994)). Several techniques have been used to prevent relapse due to co-transplantation of the malignant cells by selectively removing the malignant cells from the grafts.

In one approach, CD34-coupled immunomagnetic beads have been used to selectively isolate the hematopoietic progenitor cells from bone marrow containing malignant cells (Berenson, R. J., et al. *Blood* 77:1717 (1991); De Wynter, E. A., et al. *Stem Cells* 13:524 (1995)). Unfortunately, this procedure can only be used to remove hematopoietic progenitor cells from bone marrow containing malignant cells that do not express the CD34 antigen, since the CD34 antigen has been reported to be expressed on 9 out of 63 breast cancer, 2 out of 11 squamous cell sarcomas of the lung and 3 out of 12 small cell lung cancers (Köhler G, et al. *Blood* 86:497a (1995) (abstract)).

In another approach, the action of either an antibody and its complement (Slaper-Cortenbach, I. C. M., et al. *Exp Hematol.* 18:49 (1990)), cytotoxic drugs (Uckun, F. M., et al. *Blood* 69:361 (1987)), or a photosensitizer (Levy, J. G., et al. *Stem Cells* 13:336 (1995)) has been used to selectively kill the malignant cells. The photoinactivation of malignant cells has been successfully achieved using a variety of photosensitizers such as merocyanine-540 (MC 540) (Atzpodien, J., et al. *Cancer Res.* 46:4892 (1986); Sieber, F. *Photochem Photobiol.* 46:71 (1987)), dihematoporphyrin ether (DHE) (Atzpodien, J., et al. *Blood* 70:484 (1987)), pyrene-containing sensitizers (P12) (Fibach, E., et al. *Exp Hematol.* 18:89 (1990); Fibach, E., et al. *Leukemia Res.* 16:453 (1992)), and sulphonate aluminum phthalocyanine (AlSPc) (Singer, C. R. J., et al. *Br. J. Haematol.* 68:417 (1988)).

The relatively low cytotoxicity of the phthalocyanines (Pc) and their resistance to chemical and photochemical degradation (Chan, W. S., et al. *Br. J. Cancer* 53:255 (1986)) led to the development of new Pc photosensitizers (Oleinick, N. L., et al. *Photochem. Photobiol.* 57:242 (1993)). One of these is hydroxysiloxy-dimethylpropyl-N-dimethyl silicon phthalocyanine $(HOSiPcOSi(CH_3)_2(CH_2)_3N(CH_3)_2)$ ("Pc 4") (Oleinick, N. L., supra; Zaidi, S. I. A., et al. *Photochem. Photobiol.* 58:204 (1993)), which has been shown to effectively photoinactivate viruses (Ben-Hur, E., et al. *Photochem. Photobiol.* 62:575 (1995)), and parasites (Ben-Hur, E., et al.: Photodynamic decontamination of blood for transfusion, in Brault D, G Jori G, Ehrenberg B (eds): Photodynamic therapy of cancer II, SPIE, vol. 2325, p. 166 (1995); Gottlieb, P., et al. *Photochem. Photobiol.* 62:869 (1996)) in blood products, and mammalian cells such as V79 (a chinese hamster lung fibroblast cell line) (Zaidi, S. I. A., et al., supra).

SUMMARY OF THE INVENTION

The present invention provides a method for photoinactivating malignant cells in a cell sample. The method comprises incubating the cell sample with a concentration of Pc 4 effective to cause a substantial number of the malignant cells contained in the cell sample to absorb Pc 4 such that upon application of a sufficient dose of red light, the Pc 4 absorbed malignant cells will be photoinactivated; and applying a sufficient dose of red light to the cell sample to photoinactivate the Pc 4 absorbed malignant cells contained in the cell sample.

BRIEF DESCRIPTION OF THE FIGURES

FIGS. 1A–1E represent dose response of murine cell lines (ABE 8.1/2, FIG. 1A; BC3A, FIG. 1B; L1210, FIG. 1C; P815, FIG. 1D; WEHI-3, FIG. 1E) incubated with 15 nM Pc 4 at concentrations of $1.5 \times 10^7$ cells/mL (open circles) and $1.5 \times 10^6$ cells/mL (solid circles). The survival data represent the means±SEM of three experiments; the survival of the untreated controls was standardized to 1.0. Symbols with horizontal lines indicate the threshold levels of detection.

FIGS. 2A and 2B represent dose response of committed murine bone marrow progenitor subsets (CFU-Mk, open circle; CFU-GM, open square; CFU-Mix, solid circle; BFU-E, solid square) after incubation with 15 nM Pc 4 at concentrations of $1.5 \times 10^7$ cells/mL (FIG. 2A) and $1.5 \times 10^6$ cells/mL (FIG. 2B). The survival data represent the means±SEM of three experiments; the survival of the untreated controls was standardized to 1.0. Symbols with a horizontal line indicate the threshold levels of detection.

DETAILED DESCRIPTION OF THE INVENTION

Figure 1A:
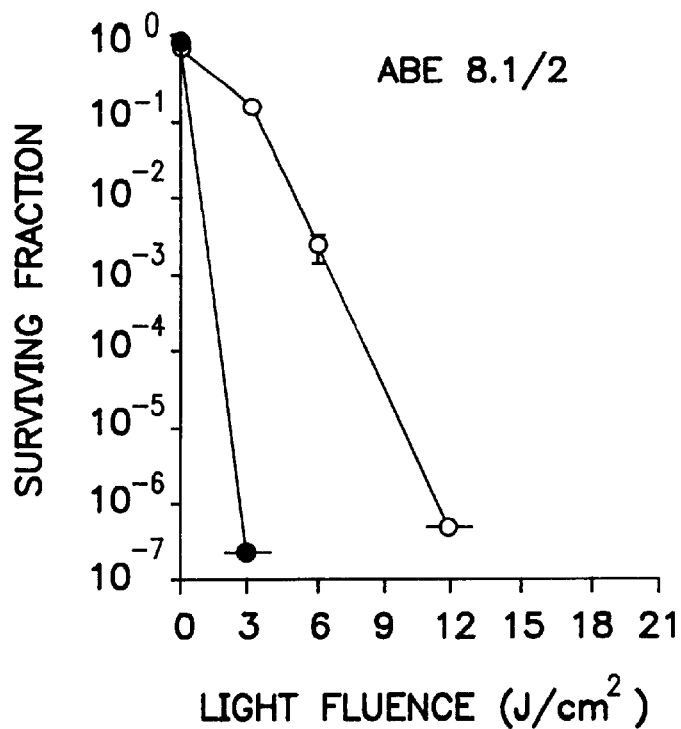

The present invention provides a method for photoinactivating malignant cells in a cell sample. The method comprises incubating the cell sample with a concentration of Pc 4 effective to cause a substantial number of the malignant cells contained in the cell sample to absorb Pc 4 such that upon application of a sufficient dose of red light, the Pc 4 absorbed malignant cells will be photoinactivated; and applying a sufficient dose of red light to the cell sample to photoinactivate the Pc 4 absorbed malignant cells contained in the cell sample.

As used herein, "cell sample" includes samples which contain hematopoietic progenitor cells (e.g., committed BM progenitor cells and pluripotent stem cells) such as bone marrow, peripheral blood and umbilical cord blood, as well as the hematopoietic progenitor cells themselves which have been isolated by positive selection (e.g. CD34 selection). In the preferred embodiment, the cell sample contains about $10^7$ to about $10^8$ cells/ml, and most preferably, about $1.5 \times 10^7$ cells/ml. "Substantial number of malignant cells" means at least 80% and preferably, 95% or greater malignant cells. "Photoinactivation" means to destroy, inactivate or render non-functional the malignant cells.

The concentration of Pc 4 is an amount effective to cause a substantial number of the malignant cells contained in the cell sample to absorb Pc 4 such that upon application of a sufficient dose of red light, the Pc 4 absorbed malignant cells will be photoinactivated. The concentration of Pc 4 is preferably about 10 nM to about 30 nM, and most preferably about 15 nM. However, higher and lower concentrations of Pc 4 may be used. At a concentration of about 15 nM, the malignant cell will absorb the Pc 4 in appropriate amounts in about 2 hours.

After Pc 4 is accumulated in the malignant cells, red light is applied to the sample at a sufficient dose to photoinactivate the Pc 4 absorbed malignant cells. As used herein, "red light" corresponds to a wavelength of light which causes Pc 4 to undergo a photochemical reaction, and may be a narrow band corresponding to the maximum absorption of Pc 4, i.e. about 670–690 nm, or a broad band (e.g. 600–700 nm) which encompasses the absorption of Pc 4. Suitable sources of light include commercially available lasers, lamps, light emitting diodes and the like. Preferably, a xenon short arc lamp (Versa Light, Medic Lightech, Ltd., Haifa, Israel) is employed. To achieve the desired wavelength of light, the lamp may be equipped with commercially available filters.

The dose of red light applied is a dose which photoinactivates the malignant cells without damaging a substantial number of the hematopoietic progenitor cells. Such a dose may be about 3 to about 20 $J/cm^2$, and preferably is about 18 $J/cm^2$. However, the actual dose will depend upon the number and type of malignant cells, and is readily determinable by one skilled in the art.

The present invention is described in the following Experimental Details Section which is set forth to aid in an understanding of the invention, and should not be construed to limit in any way the invention as defined in the claims which follow thereafter.

Experimental Details Section Materials and Methods

Animals. C57B1/6 (Ly-5.2) and B6SJ-cd45 $^b$pep $3^b$/BOY J (Ly-5.1), were obtained from The Jackson Laboratories (Bar Harbor, Me.) and were maintained in the animal facility of the New York Blood Center. After gamma-irradiation, the animals were housed in microisolator cages and provided with autoclaved food and autoclaved acidified water (pH=3) ad libitum. Preparation of bone marrow cell suspensions—Ly-5.1 mice were used as the source of donor BM. Mice (8–10 weeks old) were killed and the BM was harvested by flushing the femoral shafts with Hank's balanced salt solution (HBSS), pH 7.4. The cell suspensions were centrifuged, washed once and the cells were finally resuspended in HBSS—10% vol/vol fetal bovine serum (FBS, Gemini Bioproducts Inc., Calabasas, Calif.).

Cell lines and culture conditions. WEHI-3 (murine myelocytic leukemia), L1210 (murine lymphocytic leukemia) and P815 (murine mastocytoma) cells were grown in RPMI 1640 (GibcoBRL, Grand Island, N.Y.) supplemented with 10% FBS. BC3A (murine leukemia) cells were grown in RPMI 1640 supplemented with 10 $\mu$M β-mercaptoethanol and 10% FBS; ABE-8.1/2 (murine pre-B lymphoma) cells were grown in DMEM (GibcoBRL)—10 $\mu$M β-mercaptoethanol—10% FBS. All cell lines were obtained from the American Type Culture Collection (Rockville, Md.) and were cultured at 37° C. in a humidified 5% $CO_2$-incubator. Prior to incubation with Pc 4, the cell lines were centrifuged and resuspended in phosphate buffered saline (PBS)—10% FBS, pH 7.4.

Photosensitization. Aliquots of a 1.87 mM Pc 4 (kindly provided by Dr. M. E. Kenney) stock solution in dimethyl sulfoxide were kept at −80° C. in autoclaved brown glass vials. Immediately prior to the photosensitization, Pc4 was thawed and diluted in dimethyl formamide to yield a 10 $\mu$M working solution. Uptake and cytoxicity of Pc4 were tested on murine BM samples and it was determined that uptake was complete after two hours and that incubation with 15 nM Pc 4 resulted in marginal losses (0–15%) of the colony forming units-granulocyte macrophage (CFU-GM). Pc 4 was used at 15 nM throughout the experiments.

BM and cell line samples, were incubated with 15 nM Pc 4 for two hours at 37° C. at cell concentrations of $1.5 \times 10^7$ cells/mL. Aliquots of 1.5 mL were transferred to 24-well plates; separate plates were used for each sample.

In a second set of experiments, the cells were incubated with 15 nM Pc 4 at cell concentrations of $1.5 \times 10^6$ cells/mL. Prior to photoirradiation, the samples were centrifuged and the supernatants were aspirated and set aside. The cell concentrations were adjusted to $1.5 \times 10^7$ cells/mL by adding back an appropriate volume of the Pc 4 containing aspirates.

Photoinactivation. The light source used was a filtered xenon short arc lamp (Versa-Light, Model UV-R6G, Medic Lightech, Ltd., Haifa, Israel). It was used to deliver red light ($\lambda$ 600–700 nm) to the sensitized cells. After a 20 minute warm up period of the instrument, the distance from the light source to the bottom of the 24-well plate was adjusted to obtain a fluence rate of 26.6 $mW/cm^2$, as measured with a radiometer (Model IL 1350, International Light, Newburyport, Mass.). Samples were placed under the light source and were stirred during the irradiations. Before and after the irradiations, samples were kept in the dark.

Colony forming assays. BM samples were plated (in duplicate) in a semi-solid medium that contained IMDM (GibcoBRL), supplemented with 30% vol/vol FBS, 0.15% wt/vol deionized bovine serum albumin (Migliaccio, G., et al. *Brit. J. Haematol.* 67:129 (1987)) (Sigma, St. Louis, Mo.), 0.8% wt/vol methylcellulose, 75 $\mu$M β-mercaptoethanol (Sigma), antibiotics (100 U/mL penicillin, 100 mg/mL streptomycin, 0.25 mg/mL fungizone, GibcoBRL) and a cocktail of growth factors including: murine interleukin-3 (1% vol/vol COS-cell-derived supernatant, gift from Dr. K. Kaushansky), murine granulocyte-macrophage colony stimulating factor (1% vol/vol COS-cell-derived supernatant, gift from Dr. K. Kaushansky), recombinant human interleukin-11 (16 U/mL, gift from Genetics Institute, Cambridge, Mass.), recombinant rat stem cell factor (100 ng/mL), granulocyte colony stimulating factor (10 ng/mL), recombinant human erythropoietin (20 ng/mL, gifts from Amgen, Thousand Oaks, Calif.), and 800 U/mL murine thrombopoietin (800 U/mL, gift from Zymonetics, Seattle, Wash.). The samples were incubated at 37° C. in a humidified 5% $CO_2$-incubator and megakaryocyte colony forming units (CFU-Mk) were counted after 5 days. Blast forming units-erythroid (BFU-E), CFU-GM and mixed colonies (CFU-Mix) were counted after seven days.

Cell line samples were plated (in triplicate) in a semi-solid medium which consisted of DMEM—20% vol/vol serum (2/3 horse serum, 1/3 FBS)—3 mM glutamine—60 $\mu$M $\beta$-mercaptoethanol—0.3% wt/vol agar. The samples were incubated at 37° C. in a humidified 5% $CO_2$-incubator, and colonies consisting of more than 50 cells were counted after nine days.

Cobblestone area forming cell assay. FBMD-1 stromal cells (gift from Dr. Ploemacher) were cultured at 33° C. in a humidified 5% $CO_2$-incubator in DMEM supplemented with 3.5 mM HEPES, 2 mM glutaMax (GibcoBRL), $10^{-7}$ M sodium selenite, $10^{-4}$ M $\beta$-mercaptoethanol, 10% vol/vol fetal calf serum (Gemini Bioproducts, Inc.), 5% vol/vol horse serum and $10^{-5}$ M hydrocortisone 21-hemisuccinate (Breems, D. A., et al. *Leukemia* 8:1095 (1994); Van der Loo, J. C. M., et al. *Blood* 85:2598 (1995)). Prior to each experiment, FBMD-1 cells were harvested from log-phase cultures and fresh layers were prepared by seeding 1,000 cells into individual wells of 96-well flat bottom plates. These plates had been incubated overnight with 0.2% (wt/vol) gelatin to improve adherence of the stromal layer. The outer wells of the plates were filled with 100 $\mu$L 0.1 N NaOH to reduce infection.

The FBDM-1 layers were overlaid with the bone marrow samples in a limiting dilution setup; the first wells receiving 180,000–300,000 cells (Breems, D. A., et al., supra). Ten dilutions 2-fold apart were used for each sample with 18 replicate wells per dilution. The cells were cultured at 33° C. in a humidified 5% $CO_2$-incubator. For each sample, the fraction of wells with at least one phase-dark hematopoietic clone of at least five cells (cobblestone area) was determined weekly and cobblestone area forming cell frequencies (CAFC) were calculated using the dedicated Poison statistics program LimDil (kindly provided by Dr. Jan Hendrikx). After counting, 100 $\mu$L medium was removed from the wells and replaced with 100 $\mu$L fresh medium.

Bone marrow transplantation and chimerism assay. Two month old Ly-5.2 mice were used as recipients in the BM reconstitution assays. Whole-body irradiation was administered in a single sub-lethal dose of 6.4 Gy at a dose rate of 80 cGy/min. The irradiated recipient Ly-5.2 mice were divided into six groups. The mice in these groups received either HBSS, untreated control bone marrow, or Pc 4-sensitized BM that was photoirradiated with 0, 6, 12 or 18 J/cm², respectively. Each mouse received 250,000 donor BM cells.

Six months after transplantation, peripheral blood was obtained by tail-vein puncture and 40 $\mu$L samples were aliquoted into tubes that contained the following antibody cocktails. The first tube contained 4 $\mu$L of phycoerythrin (PE) conjugated anti-Ly-5.1 antibody (CD45.1, kind gift from Dr. JoséCarlos Segovia) and 1 $\mu$L of fluorescein (FITC) conjugated anti-B220 antibody (B cells; Pharmingen, San Diego, Calif.), the second tube contained 4 $\mu$L anti-Ly-5.1$^{PE}$ and 1 $\mu$L of anti-CD3$^{FITC}$ (T cells; Pharmingen), and the third tube contained 4 $\mu$L anti-Ly-5.1$^{PE}$ and 1 $\mu$L of anti-Gr-1$^{FITC}$ (granulocytes; Pharmingen). Following a 20 minute incubation at room temperature, 2 mL of FACS Lysing Solution (Becton Dickinson (BD), San Jose, Calif.) was added to each sample followed by gentle mixing. After 10 minutes the samples were centrifuged and the pellets were resuspended in 3 mL PBS. After centrifugation, the washed pellets were resuspended in 2% vol/vol formalin—PBS pH 7.4 and the samples were analyzed by flow cytometry within 3 hours after staining.

Uptake of Pc 4. Following a two hour incubation at 37° C. with 15 nM Pc 4, cell line and BM samples were analyzed for Pc 4 uptake by flow cytometry. BM samples were first incubated with anti-c-kit$^{PE}$ (Pharmingen) and anti-Sca-1$^{FITC}$ (Pharmingen), to allow analysis of the Pc 4 uptake in the committed progenitor fraction (c-kit$^+$,Sca-1$^-$) and the pluripotent stem cell fraction (c-kit$^+$,Sca-1$^+$) (Li, C. L. and G. R. Johnson *Blood* 85:1472 (1995)). Following a 20 minute incubation on ice, and two subsequent washes, the samples were incubated with 15 nM Pc 4. The relative Pc 4 uptake was calculated by subtracting the mean fluorescence signals of the untreated control samples from the mean Pc 4 fluorescence signals.

In mixing experiments, aliquots of Ly-5.2 BM and cell lines samples were mixed at different ratios. The combined cell concentration of each sample was $1.5 \times 10^7$ cells/mL. Prior to the mixing of the samples, the bone marrow cells were first stained with anti-c-kit$^{PE}$ to allow analysis of the Pc 4 uptake in the committed progenitor subset (c-kit$^+$). The cell lines were stained with anti-Ly-5.1$^{FITC}$. This treatment allowed clear resolution of the relatively small ABE-8.1/2 and BC3A cells from the bone marrow granulocytes. Immediately prior to the analyses, propidium iodide (PI, 0.5 $\mu$g/mL) was added to the samples to allow exclusion of dead cells (PI$^+$) from the analyses. The samples were analyzed in a FACStar$^{PLUS}$ (BD) that was equipped with an argon ion laser tuned to 488 nm (200 mW) and a dye laser tuned to 610 nm (300 mW). FITC, PE, PI and Pc 4 fluorescence emissions were collected through 530/30, 575/42, 660/10, 670/10 nm band pass filters, respectively.

Statistics. All assays were performed in triplicate unless mentioned otherwise. Data are expressed as mean values±standard error of the mean (SEM). Survival data are presented as surviving fractions relative to the surviving fractions of the untreated controls. The significance of the differences between experimental values was assessed by means of the Student's t-test.

Cell size. Microscopic measurements of at least 20 cells were performed using a calibrated micrometer. To determine the cell size of the BM progenitor subsets, the c-kit$^+$,Sca-1$^-$ and c-kit$^+$,Sca-1$^+$ fractions were sorted. The sorted cells were centrifuged and the pellets were resuspended in a 20 $\mu$l of HBBS. Samples were deposited onto microscope slides and covered with a cover slip. Cell diameters of 7.7±0.2 (c-kit$^+$,Sca-1$^+$), 8.4±0.3 (c-kit$^+$,Sca-1$^-$), 10.9±0.2 (BC3A), 11.1±0.2 (ABE-8.1/2), 13.0±0.3 (L1210), 14.2±0.3 (P815), 15.0±0.4 $\mu$m (WEHI-3) were obtained.

Results

Figure 1B:
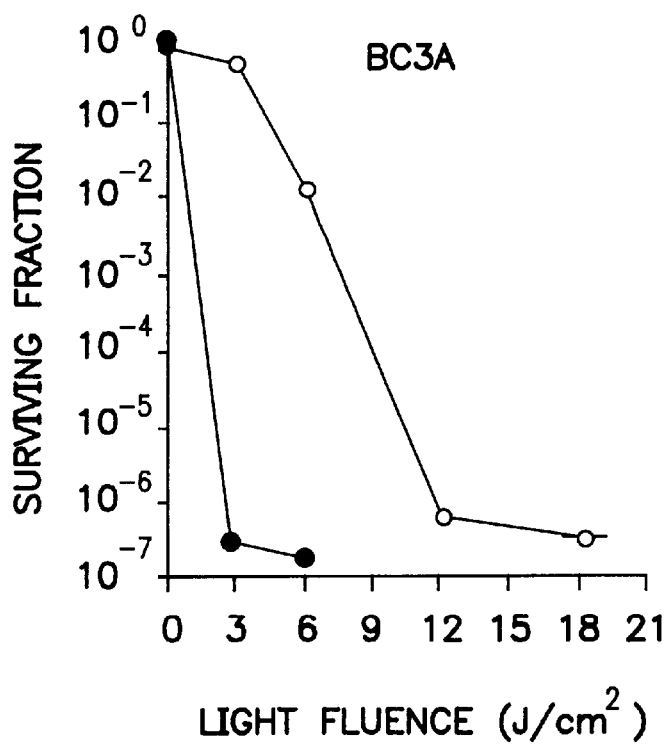

Photosensitivity of cell lines. The efficiency of photoinactivation by Pc 4 of murine cells was tested using a variety of cell lines. Because it had previously been reported that the cell concentration could affect the efficiency of photoinactivation (Fibach, E., et al. *Exp Hematol.* 18:89 (1990); Lemoli, R. M., et al. *Blood* 81:793 (1993)), it was decided to test the efficacy of the procedure at two cell concentrations. After incubation with 15 nM Pc 4 at $1.5 \times 10^7$ cells/mL, the surviving fractions of the cell lines ranged from 0.73–1.00. Irradiation of the sensitized cells with increasing fluences of red light resulted in a progressive loss of the colony forming abilities of the cell lines (FIG. 1). For samples that were incubated with Pc 4 at $1.5 \times 10^7$ cells/mL, the small BC3A and ABE 8.1/2 cells were photoinactivated to below the detection levels (surviving fractions=$2-5 \times 10^{-7}$) after receiving fluences of 12 J/cm², while the intermediately sized L1210 cells required 18 J/cm². This fluence was insufficient to completely photoinactivate the larger P815 and WEHI-3 cells; surviving fractions were $5.3 \pm 2.6 \times 10^{-4}$, and $3.8 \pm 0.07 \times 10^{-6}$, respectively.

Pc 4 photoinactivation proved more efficient when the cells were incubated at $1.5 \times 10^6$ cells/mL. The cell lines could be photoinactivated to below the detection levels with fluences of 3 J/cm$^2$ (ABE-8.1/2), 6 J/cm$^2$ (BC3A, L1210, P815) and 12 J/cm$^2$ (WEHI-3), respectively.

Photosensitivity of committed BM progenitor cells. For BM samples incubated with Pc 4 at 1.5×10$^7$ cell/mL, all committed progenitor subsets proved resistant to a fluence of 3 J/cm$^2$. However, after photoirradiation with a maximum fluence of 18 J/cm$^2$, the colony forming abilities of the CFU-Mk, CFU-GM, CFU-Mix, BFU-E were reduced to 8.4±2.2×10$^{-2}$, 3.8±0.7×10$^{-2}$, 1.8±5.0×10$^{-3}$ and <3.0×10$^{-3}$ of the untreated controls (FIG. 2A), respectively. The committed progenitors were also found to be more sensitive to Pc 4 photoinactivation after incubation with 15 nM Pc 4 at 1.5×10$^6$ cells/mL (FIG. 2B). Photoinactivation to below the detection levels was found for the fluences of 3 J/cm$^2$ (CFU-Mix and BFU-E) and 6 J/cm$^2$ (CFU-Mk and CFU-GM), respectively.

Figure 3:
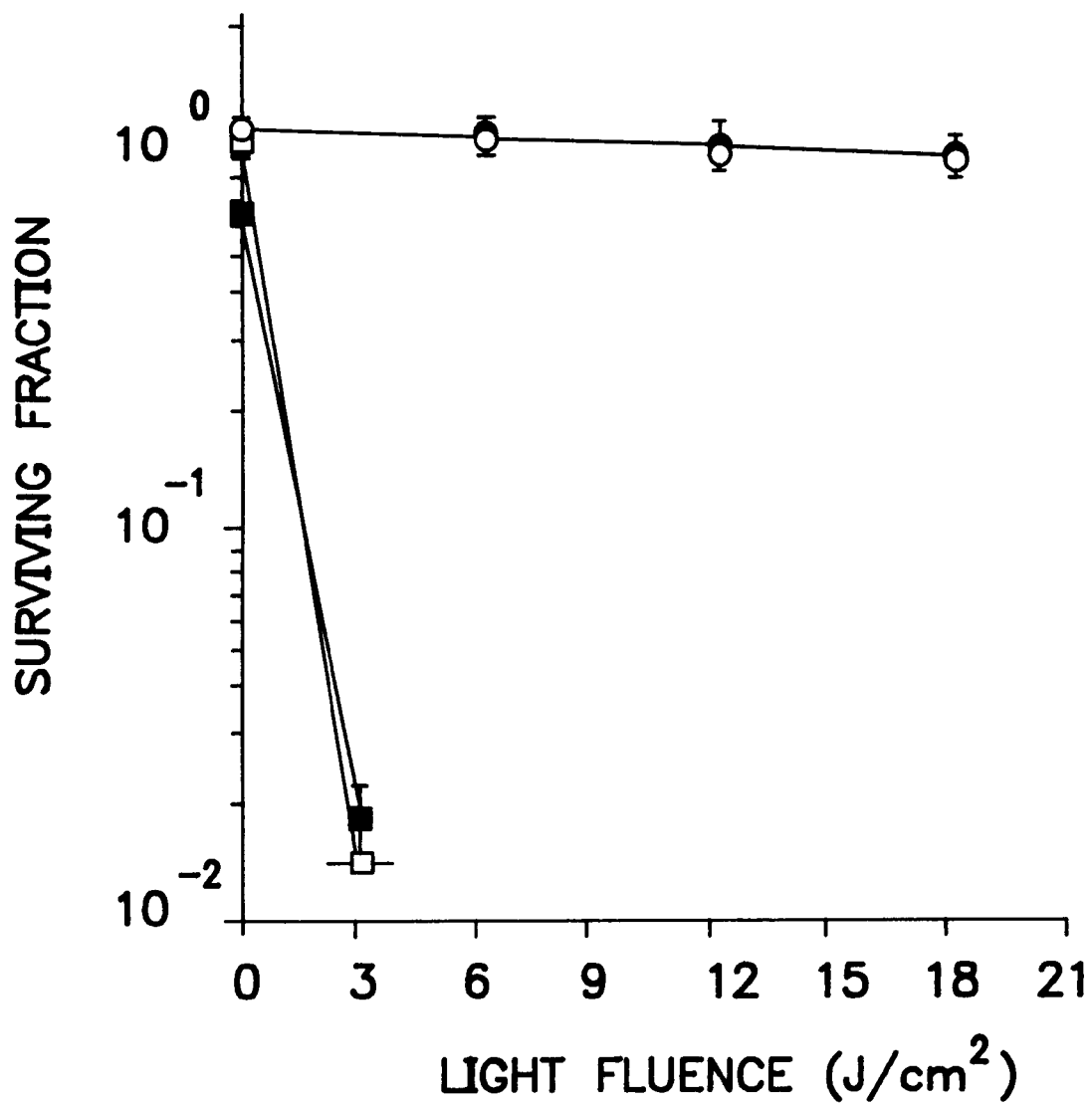
FIG. 3 represents dose response of murine hemopoietic stem cells, as measured by cobble stone forming cell (CAFC) assay, after incubation with 15 nM Pc 4 at concentrations of $1.5 \times 10^7$ BM cells/mL (circles) and $1.5 \times 10^6$ cells/mL (squares). The data represent the means±SEM of four individual experiments; the survival of the untreated controls was standardized to 1.0. The symbols with a horizontal line indicates the threshold levels of detection. The CAFC frequencies of the samples that were incubated with Pc 4 at $1.5 \times 10^7$ cells/mL and irradiated with 6 J/cm² (p=0.58), 12 J/cm² (p=0.40), 18 J/cm² (p=0.26) were found to be not significantly lower than CAFC frequencies of the untreated samples.

Photosensitivity of pluripotent stem cells—in vitro assay. To evaluate the photosensitivity of the most immature cells in the BM, two different assays were performed: the in vitro CAFC assay and the analysis of chimerism in peripheral blood leukocytes after bone marrow transplantation. The results from two CAFC assays (FIG. 3) revealed that the CAFC frequencies of the photosensitized samples (incubated with Pc 4 at 1.5×10$^7$ cells/mL) were not affected after irradiation. The relative CAFC frequencies on day 28 of samples that were irradiated with 18 J/cm$^2$, were 0.91 (p=0.69) and 0.92 (p=0.78) indicating that there was no significant photoinactivation of the pluripotent stem cells.

However, the survival of BM samples was greatly reduced after incubation with Pc 4 at 1.5×10$^6$ cells/mL. Following irradiation with a fluence of 3 J/cm$^2$, the relative CAFC day 28 frequencies were 0.018 and below the detection limit of 0.014, and it was therefore decided not to perform the transplantation assay following incubation at 1.5×10$^6$ cells/mL.

Photosensitivity of plurinotent stem cells—in vivo assay. The long term repopulating (LTR) ability of photoirradiated immature BM progenitor cells was tested using Ly-5.1 BM cells that were transplanted into irradiated Ly-5.2 mice. In a pilot experiment, lethally irradiated recipients (8.5 Gy total body gamma-irradiation) received either 70,000 or 250,000 untreated or treated donor BM cells (18 J/cm2, 15 nM Pc 4, 1.5×10$^7$ cells/mL) per group (n=3). All mice that received 70,000 cells died within one month, while most of the mice that received 250,000 donor cells developed high levels of Ly-5.1 chimerism (>70% after 4 months) in the peripheral blood granulocytes, T cells and B cells (data not shown).

Figure 4:
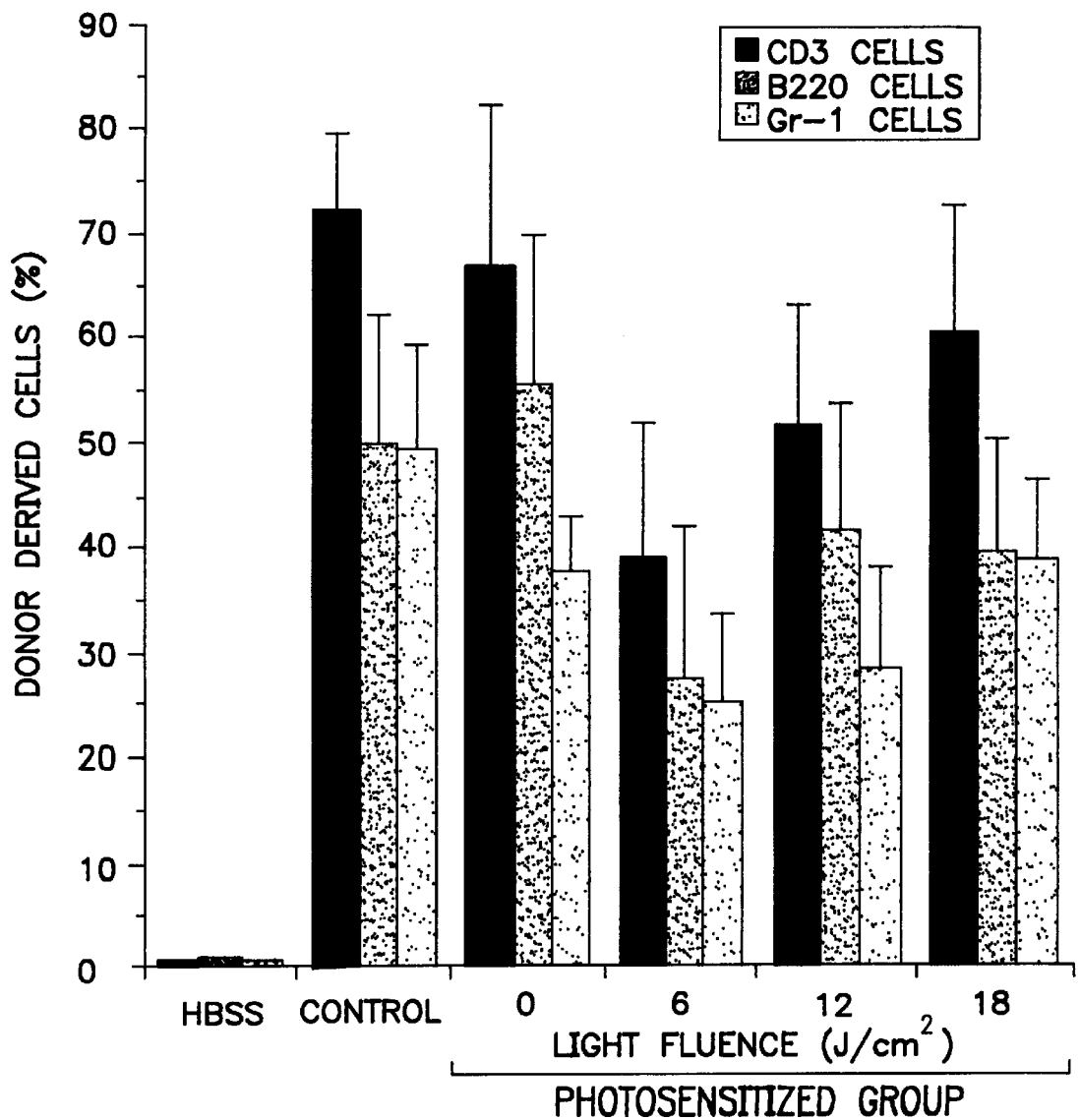
FIG. 4 represents chimerism levels, six months after transplantation, of leukocyte subsets in recipient Ly-5.2 mice after transplantation with 250,000 Ly-5.1 donor BM cells. The data represent the mean chimerism values±SEM from an experiment in which the recipient mice were non-lethally irradiated (6.4 Gy). Mice were injected with either HBSS, (untreated) control BM cells or BM cells that were incubated with 15 nM Pc 4 at $1.5 \times 10^7$ cells/mL followed by exposure to increasing fluences of red light. The CD3 (first box), B220 (second box), Gr-1 positive cells (third box), represent donor stem cell derived T cells, B cells and granulocytes, respectively.

In another experiment, sub-lethally irradiated Ly-5.2 mice were transplanted with 250,000 photoirradiated Ly-5.1 bone marrow cells. Two months after the transplants, several mice from different groups died: 1/5 in the control group that received only HBSS and 1/6 in the groups that received Pc 4 and fluences of 0, 6 and 18 J/cm$^2$, respectively. Six months after transplantation, significant levels of chimerism were found in the peripheral leukocytes of all recipient mice (FIG. 4). The differences between the chimerism levels of the group that received untreated BM cells and the group that received BM cells that had been incubated with Pc 4 and irradiated with 18 J/cm$^2$ were found to be not significant, indicating that (1) the LTR ability of the pluripotent stem cells was not affected by the photoinactivation procedure, (2) the loss of 2–3 logs of committed progenitor cells did not significantly affect engraftment. The chimerism levels for the groups that received untreated control bone marrow cells and bone marrow cells that were photoinactivated with 18 J/cm$^2$ were 0.72±0.07, 0.60±0.12 (T cells, p=0.42), 0.50±0.12, 0.39±0.11 (B cells, p=0.53) and 0.49±0.01, 0.38±0.08 (granulocytes, p=0.42), respectively.

Figure 5:
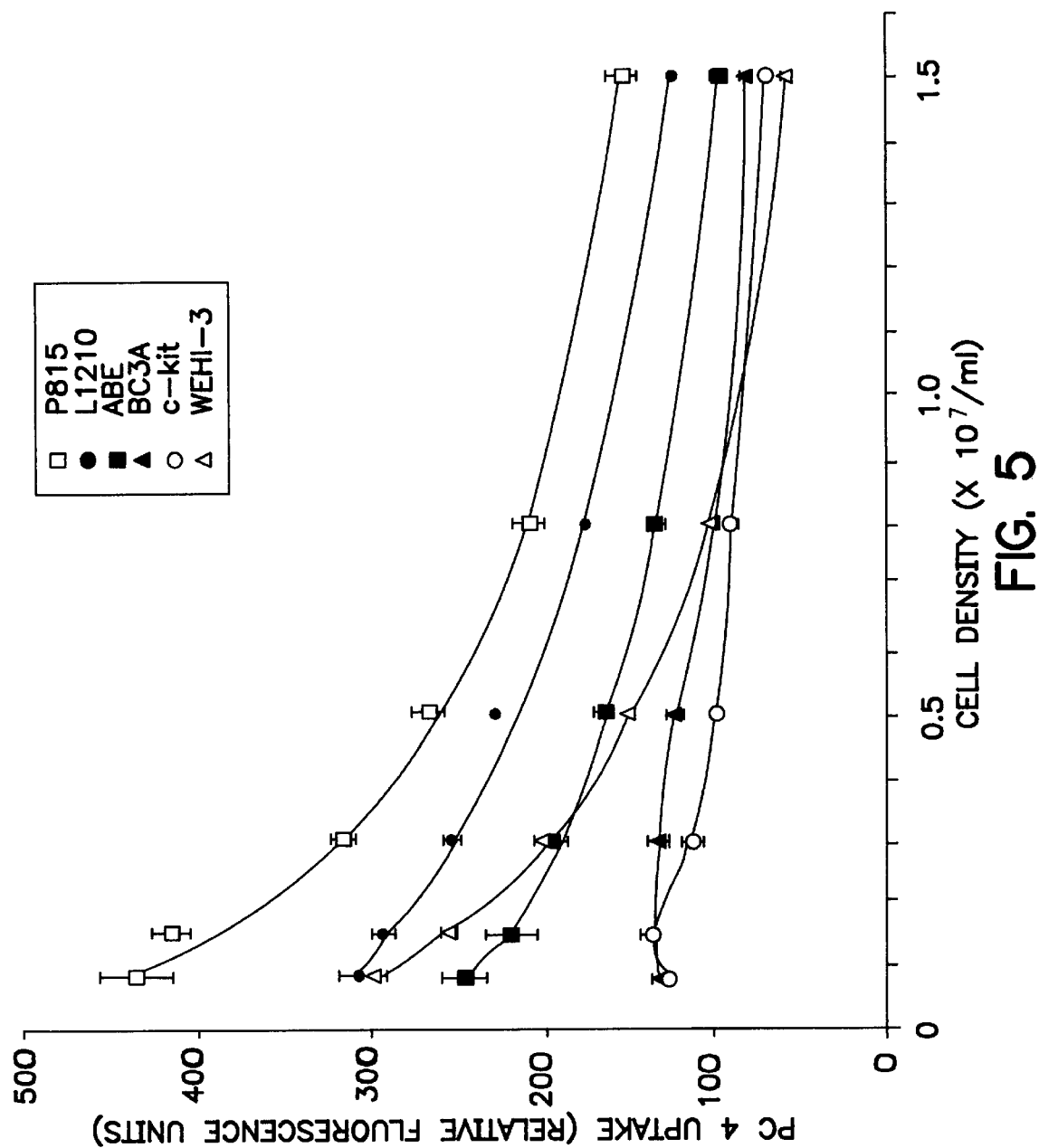
FIG. 5 represents the relative Pc 4 uptake as a function of cell concentration after incubation with 15 nM Pc 4. The fluorescence data represent the means±SEM of the three experiments; the lines were manually fitted to the data points. Cells (P815, open square; L1210, solid circle; ABE, solid square; BC3A, solid triangle; c-kit, open circle; WEHI-3, open triangle) were incubated at concentrations ranging from $8.0 \times 10^5 – 1.5 \times 10^7$ cells/mL. The Pc 4 values represent the relative mean fluorescence values of the Pc 4-treated cells minus the mean fluorescence values of the untreated cells. BM cells that stained positive with the anti-c-kit antibody were regarded as committed BM progenitor cells.

Differential uptake of Pc 4 by cell lines and bone marrow progenitor subsets. The relative Pc 4 contents of the cell lines and bone marrow progenitor subsets were analyzed by flow cytometry (Fibach, E., et al. *Leukemia Res.* 16:453 (1992)) in search of an explanation for the differential photosensitivity of the BM progenitors (c-kit$^+$) and the cell lines (FIG. 5). For all cell types, the uptake of Pc 4 was inversely correlated with the cell concentration during incubation. The Pc 4 uptake in the BC3A and the BM progenitor cells reached a plateau at cell concentrations of 8.0×10$^5$ cells/mL. Increasing the cell concentrations from 8.0×10$^5$ to 1.5×10$^7$ cells/mL resulted in a 1.6-fold (BC3A), 1.8-fold (BM progenitors), 2.5-fold (ABE-8.1/2, L1210), 2.8-fold (P815), and 5.1-fold (WEHI-3) reduction of Pc 4 uptake, respectively.

The cellular Pc levels for cells incubated at 1.5×10$^7$ and 1.5×10$^6$ cells/mL (Table 1), revealed a close correlation with the cell size; the WEHI-3 cells being the exception. Despite the significant differences in photosensitivity, the difference in Pc 4 content (at 1.5×10$^7$ cells/mL) between the pluripotent stem cells and the committed progenitors was found to be not significant (p=0.26), and the differences between the committed progenitors and the BC3A and ABE-8.1/2 were found to be not significant (p=0.29) and not quite significant (p=0.07), respectively.

When the data were corrected for the cell volume, it was found that the differences in cellular Pc 4 concentration among the BC3A, ABE-8.1/2, L1210 and P815 cells were marginal. The BM fractions containing the committed progenitors and the pluripotent stem cells were found to contain almost twice the cellular Pc 4 concentration of the cell lines.

For each cell type, the photosensitivity correlated with the cellular Pc 4 fluorescence. However, when comparing cell types, there appeared to be no correlation between photoinactivation and photosensitizer uptake (Fibach, E., et al. *Leukemia Res.* 13:1009 (1989)). In fact, the cells with highest Pc 4 fluorescence, i.e., the c-kit$^+$,Sca-1$^+$BM fraction containing the pluripotent stem cells, were found to be the least sensitive to Pc 4 photoinactivation.

Addition of verapamil, a known inhibitor of the multidrug resistance (mdr) pump to the BM samples during incubation with Pc 4 did not increase the uptake of Pc 4 (data not shown). This result indicated that Pc 4 is not a substrate for the multidrug resistance pump which is expressed in murine pluripotent stem cells (Zijlmans, J. M. J. M., et al. *Proc Natl Acad Sci USA* 92:8901 (1995)).

Uptake of Pc 4 in cell mixtures. BM and cell lines were mixed to simulate clinical samples and Pc 4 uptake was also used to evaluate the differential Pc 4 photoinactivation (Table 2), using the results described in the previous paragraphs. The cellular uptake of Pc 4 by the cell lines and the BM progenitors (c-kit$^+$) was found to increase as the fraction of BM cells in the mixtures was increased from 0.5 to 0.95.

In all mixtures, the Pc 4 uptake of the BM progenitor fractions was lower, though not significantly (p>0.07), than when the BM samples were incubated without the cell lines. In contrast, BC3A, L1210, P815 and WEHI-3 cells contained more Pc 4 in the mixtures than if these cells were incubated at 1.5×10$^7$ cells/mL without BM. The Pc 4 uptake in the ABE-8.1/2 cells in mixtures that contained a BM fraction<0.9 was lower than the uptake of ABE-8.1/2 cells that were incubated without BM. These data indicated that ABE-8.1/2 would be less effectively photoinactivated in mixtures that contained a BM fraction<0.9 and that the other four cell lines would be photoinactivated more effectively in mixtures with BM cells. Whether this would lead to complete photoinactivation of the P815 and WEHI-3 cells could not be predicted from the data in Table 1 as the Pc 4 concentrations in the mixed samples were lower than in the cells after incubation at 1.5×10$^6$ cells/mL without BM.

Discussion

The data presented above confirm the preferential photoinactivation of cancer cells over committed BM progenitors (Pretti, R. A., et al. *J. Hematotherapy* 4:246 (1995) (abstract)) that was reported for human cells. In addition, they clearly indicate that the pluripotent hemopoietic stem cells, which are of the utmost importance for transplantation, are not damaged by Pc 4 phototreatment.

After incubation with 15 nM Pc 4 at $5 \times 10^6$ cells/mL and irradiation with 8 J/cm$^2$, the surviving fractions of human cells were reported to be 1.0 (CFU-GM), 0.9 (BFU-E), and $<10^{-5}$ (SK-BR3, HL-60), respectively. A direct comparison of the human and murine survival data was not possible due to the different cell concentrations that were used during the incubation with Pc 4. However, from the data in FIG. 1 it could be assumed that the murine survival data for incubations at $5 \times 10^6$ cells/mL would be similar to the human data.

Used under optimal conditions (15 nM—$1.5 \times 10^7$ cells/mL—18 J/cm$^2$), Pc 4 reduced the surviving fractions of committed progenitors subsets, CFU-GM and BFU-E, to 0.084 and <0.003. Other photosensitizers reduced the surviving fractions of CFU-GM and BFU-E to 0.6 and 0.7 (P12) (Fibach, E., et al. *Exp Hematol.* 18:89 (1990)), 0.17 and 0.04 (MC-540) (Gulliya, K. S. and S. Pervaiz *Blood* 73:1059 (1989)), 0.18 and 0.14 (MC540) (Atzpodien, J., et al. *Cancer Res.* 46:4892 (1986)), 0.29 and 0.47 (DHE) (Atzpodien, J., et al. *Blood* 70:484 (1987)), 0.05 and 0.10 DHE (Lemoli, R. M., et al. *Blood* 81:793 (1993)), 0.04 and 0.05 (benzoporphyrin derivative monoacid ring A, BPD-MA) (Lemoli, R. M., et al. *Blood* 81:793 (1993)), 0.60 and no BFU-E data (AlSPc) (Singer, C. R. J., et al. *Br. J. Haematol.* 68:417 (1988)), respectively, under conditions leading to 4–5 log$_{10}$ reduction of cancer cell survival. Thus, application of Pc 4 proved to be significantly more phototoxic towards the CFU-GM and BFU-E.

However, no adverse affect on the survival and LTR of the pluripotent stem cells was found after photoirradiation (at $1.5 \times 10^7$ cells/mL) with a fluence of 18 J/cm$^2$. This resulted in a selective photoinactivation of >6 log$_{10}$ for ABE-8.1/2, BC3A and L1210, of 5 log$_{10}$ for WEHI-3 and >3 log$_{10}$ for P815. Incubation at $1.5 \times 10^6$ cells/mL resulted in a photoinactivation of the stem cells (CAFC) of approximately 2 log$_{10}$, and this dramatically reduced the selectivity of Pc 4 photoinactivation towards the cell lines to approximately 5 log$_{10}$ for ABE-8.1/2 and BC3A, 4 log$_{10}$ for WEHI-3, 3 logs for P815, and <1 log$_{10}$ for L1210. Thus, for selective photoinactivation, incubation at $1.5 \times 10^7$ cells/mL appeared optimal. Used under these conditions, Pc 4 yielded similar results as DHE and BPD-MA (Lemoli, R. M., et al. *Blood* 81:793 (1993)), but compared favorable to MC 540 (Sieber, F. *Photochem Photobiol.* 46:71 (1987)) which resulted in 1 log$_{10}$ depletion of murine pluripotent stem cells. Although it was not extensively studied, the uptake data in the presence of verapamil indicated that Pc 4 was not a substrate for the mdr-pump in the pluripotent stem cells. Thus for application with samples containing mdr$^+$ leukemic cells, Pc 4 compared favorable to BPD-DA (Lemoli, R. M., et al. *Blood* 81:793 (1993)) and the cationic photosensitizer benzochlorin (Kessel, D., et al. *Photochem. Photobiol.* 60:61 (1994)).

The attempts to explain the selectivity of Pc 4 photoinactivation by differential uptake of Pc 4 (Table 1) failed. However, (with exception of WEHI-3) the correlation between cell size and photosensitizer uptake that was reported for hematoporphyrin derivative (HPD) (Böhmer, R. M., et al. *Cancer Res.* 45:5328 (1985)) was confirmed. Furthermore, increased uptake resulted in increased photosensitivity for each cell type as was reported for Photofrin (Williams, R. D., et al. *Photochem. Photobiol.* 46:733 (1987)). In the latter study, uptake had been found to linearly correlate with cell death when low fluences were used and cell survival ranged from 100–1%.

No correlation was found between photosensitivity and Pc 4 content or Pc 4 concentration among the tested cell types. This result is in agreement with the results from photoinactivation experiments with P12 (Zijlmans, J. M. J. M., et al. *Proc Natl Acad Sci USA* 92:8901 (1995)) and Photofrin (Blais, J., et al. *J. Photochem. Photobiol. B: Biol.* 27:225 (1995)). In these studies marginal differences in photoinactivation were found between cell types despite significant differences in photosensitizer uptake. When corrected for cell volume, there also was no apparent correlation between Pc 4 concentration and photosensitivity. Most strikingly, the pluripotent stem cell fraction was found to be the least photosensitive while the cells contained the highest concentration of Pc 4. This finding was in conflict with the assumption that during low power irradiations, a higher photosensitizer concentration should lead to a higher concentration of triplet state photosensitizer molecules which in turn translates to higher concentrations of reactive oxygen species and subsequently to more photodamage (Keij, J. F., et al. *Photochem. Photobiol.* 60:503 (1994)). Taken together, the data indicate that other factors, such as localization of photosensitizer molecules at specific damage-sensitive sites and the capacity to repair photodamage (Gomer, C. J. *Photochem. Photobiol.* 54:1093 (1991)), determine photosensitivity among different cell types.

When mixed with BM, previous studies with AlSPc (Singer, C. R. J., et al. *Br. J. Haematol.* 68:417 (1988)) (BM fraction=0.99) had shown that cell lines were photoinactivated as effectively as unmixed cell lines, while studies with MC540 (Meagher, R. C., et al. *Cancer Res.* 49:3637 (1989)) (BM fraction=0.95–0.99), indicated that cell lines were more effectively inactivated in mixtures. Uptake data from the mixing experiments (Table 2), revealed that Pc 4 uptake by the cell lines was proportional to the fraction of BM cells in the mixtures. Cell line fractions in the mixtures contained more Pc 4 than when the unmixed cell lines were incubated at $1.5 \times 10^7$ cells/mL; ABE-8.1/2 being the exception. In contrast, Pc 4 uptake by committed progenitor cells was inversely proportional to the BM fraction in the mixtures and uptake was equal or lower than when unmixed BM cells were incubated alone. It can therefore be concluded that in BM mixtures the cell lines would be more effectively photoinactivated and that progenitor cells would suffer less photodamage.

For clinical applications of Pc 4, these results would imply that photoinactivation with Pc 4 for purging purposes would be most effective with samples from patients in remission. Secondly, if photoinactivation were to be used in combination with positive selection of stem cells, photoinactivation should precede CD34-selection if the cancer cells also express the CD34 antigen. In cases where the cancer cells do not express the CD34 and the fraction of cancer cells in the sample is high, it could be advantageous to perform the CD34-selection first.

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

TABLE 1

Uptake of Pc 4 as a function of cell type and cell concentration

| cell type | Pc 4 content (Mean fluorescence/cell ± SEM) cells/ml during incubation | | cell volume ($\mu m^3$) | Pc 4 content (Mean fluorescence/$\mu m^3$) cells/ml during incubation | |
|---|---|---|---|---|---|
| | $1.5 \pm 10^7$ | $1.5 \pm 10^6$ | | $1.5 \pm 10^7$ | $1.5 \pm 10^6$ |
| pluripotent stem cells | 54 ± 6.9 | 109 ± 6.5 | 239 | 0.23 | 0.50 |
| progenitor cells | 68 ± 8.2 | 136 ± 7.8 | 310 | 0.22 | 0.44 |
| BC3A | 80 ± 5.5 | 137 ± 11.3 | 678 | 0.12 | 0.20 |
| ABE-8.1/2 | 95 ± 7.6 | 218 ± 29.0 | 716 | 0.13 | 0.30 |
| L1210 | 124 ± 4.2 | 291 ± 14.0 | 1150 | 0.11 | 0.25 |
| P815 | 152 ± 17.2 | 414 ± 21.5 | 1499 | 0.10 | 0.28 |
| WEHI-3 | 57 ± 4.7 | 296 ± 8.5 | 1767 | 0.03 | 0.17 |

TABLE 2

Uptake of Pc 4 in mixtures of BM and cell lines

| cell mixture | Pc 4 content (Mean fluorescence/cell) in c-kit+ BM/cell line mixtures fraction of BM in mixtures | | | | |
|---|---|---|---|---|---|
| | 0.50 | 0.70 | 0.80 | 0.90 | 0.95 |
| BM/BC3A | 48/104 | 53/26 | 61/138 | 68/153 | 64/166 |
| BM/ABE-8.1/2 | 48/74 | 52/86 | 49/91 | 55/95 | 62/100 |
| BM/L1210 | 35/153 | 43/189 | 48/210 | 54/242 | 60/260 |
| BM/P815 | 45/205 | 51/241 | 64/270 | 63/312 | 64/335 |
| BM/WEHI-3 | 30/106 | 38/140 | 46/164 | 58/204 | 65/229 |

What is claimed:

1. A method for photoinactivating malignant cells in a bone marrow cell sample containing malignant cells, said method comprising incubating the bone marrow cell sample with hydroxysiloxydimethyl-propyl-N-dimethyl silicon phthalocyanine (Pc4) at a concentration of 10–30 nM for a period of time effective to cause a substantial number of the malignant cells contained in the bone marrow cell sample to absorb Pc4; and applying a sufficient dose of red light to the cell sample to photoinactivate the Pc4 absorbed malignant cells contained in the bone marrow cell sample.

2. The method of claim 1, wherein the cell sample contains $10^7$ to $10^8$ total cells/ml.

3. The method of claim 2, wherein the cell sample contains about $1.5 \times 10^7$ total cells/ml.

4. The method of claim 1, wherein the concentration of Pc 4 is about 15 nM.

5. The method of claim 1, wherein the red light applied has a wavelength of 600–700 nm.

6. The method of claim 1, wherein the dose of red light applied is 3 to 20 J/cm$^2$.

7. The method of claim 6, wherein the dose of red light applied is about 18 J/cm$^2$.

* * * * *